United States Patent [19]
Battistini et al.

[11] Patent Number: 5,849,710
[45] Date of Patent: Dec. 15, 1998

[54] SUBSTITUTED INDOLYLMETHYLENE-OXINDOLE ANALOGUES AS TYROSINE KINASE INHIBITORS

[75] Inventors: Carlo Battistini, Novate Milanese; Dario Ballinari, S. Donato Milanese; Antonella Ermoli, Buccinasco; Sergio Penco, Milan; Sergio Vioglio, Cusano Milanino, all of Italy

[73] Assignee: Pharmacia & Upjohn S.p.A., Milan, Italy

[21] Appl. No.: 750,208

[22] PCT Filed: Mar. 14, 1996

[86] PCT No.: PCT/EP96/01165

§ 371 Date: Dec. 4, 1996

§ 102(e) Date: Dec. 4, 1996

[87] PCT Pub. No.: WO96/32380

PCT Pub. Date: Oct. 17, 1996

[30] Foreign Application Priority Data

Apr. 7, 1995 [GB] United Kingdom .................... 9507298

[51] Int. Cl.⁶ .......................... A01N 43/38; A61K 31/40; C07D 209/14; C07D 209/34
[52] U.S. Cl. .............................. 514/18; 514/19; 514/323; 514/414; 514/418; 546/201; 548/455; 548/469; 548/486; 548/490
[58] Field of Search ................................ 514/18, 19, 323, 514/414, 418; 546/201; 548/455, 469, 486, 490

[56] References Cited

U.S. PATENT DOCUMENTS 5,409,949  4/1995  Buzzetti et al. ................. 514/414

FOREIGN PATENT DOCUMENTS 9113055  9/1991  Italy .
9301182  1/1993  Italy .

*Primary Examiner*—Johann Richter
*Assistant Examiner*—Jane C. Osewcki
*Attorney, Agent, or Firm*—Oblon, Spivak, McClelland, Maier & Neustadt, P.C.

[57] ABSTRACT

The present invention relates to indol-3-ylmethylene-2-oxindole derivatives which are useful as tyrosine kinase inhibitors. The compounds are suitable for use as anti-proliferative agents, anti-metastatic agents, anti-cancer agents, and in the control of angiogenesis and in inhibiting the development of atheromatous and an immunomogulating agents.

12 Claims, No Drawings

SUBSTITUTED INDOLYLMETHYLENE-OXINDOLE ANALOGUES AS TYROSINE KINASE INHIBITORS

This application is a 371 of PCT/EP96/01165 filed Mar. 14, 1996.

The present invention relates to new derivatives of substituted indolylmethylene-oxindoles, to a process for their preparation, to pharmaceutical compositions containing them and to their use as therapeutic agents, in particular in treating a patient in need of tyrosine kinase inhibition.

International applications WO91/13055 and WO93/01182 disclose indolylmethylene-oxindole derivatives endowed with high in-vitro tyrosine kinase inhibiting activity. However, such methylen-oxindole derivatives, similarly to other known tyrosine kinase inhibitors, are characterized by high lipophylicity, low aqueous solubility and consequently low bioavailability.

However, the task to combine in the same molecule a high tyrosine kinase inhibiting activity and adequate hydrosolubility cannot be achieved by merely introducing hydrophilic groups into the structure of in-vitro active tyrosine kinase inhibitors, as this strategy results in most cases in a significant loss of inhibitory activity. Indeed, as known in the art, the therapeutic efficacy of all drugs is strongly influenced by different parameters that can affect their bioavailability. Object of the present invention is therefore to provide novel indolylmethylene-oxindole compounds endowed with improved bioavailability.

Accordingly, the present invention provides novel indol-3-ylmethylene-2-oxindole derivatives having the following general formula (I)

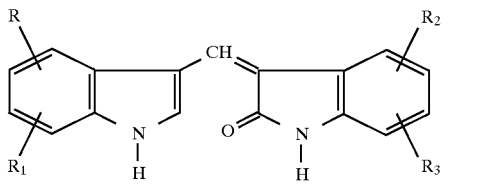

wherein
one or two of R, $R_1$, $R_2$ and $R_3$ are a substituent selected independently from:

a) a —X—$(CH_2)_m$—$NH_2$, —X—$(CH_2)_m$—$NR_4R_5$, or —X—$(CH_2)_m$—$NHR_6$ group, in which X is —O—, —S— or —NH—, m is an integer of 1 to 4, one of $R_4$ and $R_5$ is hydrogen or $C_1$–$C_6$ alkyl and the other is $C_1$–$C_6$ alkyl or $R_4$ and $R_5$ taken together with the nitrogen atom to which they are linked form a $C_4$–$C_7$ saturated heteromonocyclic ring, and $R_6$ is $C_2$–$C_6$ alkanoyl or the terminal carbonyl group of a peptidyl residue containing from 1 to 3 aminoacids wherein the terminal amino group is either free or in a protected form or in an alkylated form to provide a —$NR_4R_5$ group in which $R_4$ and $R_5$ are as defined above;

b) a —NHC(NH)$NH_2$, —NHC(NH)$NR_4R_5$, —NHC(NH)$NHR_6$, —N=CH—$NH_2$, —N=CH—$NR_4R_5$ or —N=CH—$NHR_6$ group in which $R_4$, $R_5$ and $R_6$ are as defined above;

c) a —X—$(CH_2)_m$—$COR_7$ group wherein X and m are as defined above, $R_7$ is hydroxy, amino, $C_1$–$C_6$ alkoxy or —$NR_4R_5$ in which $R_4$ and $R_5$ are as defined above, or $R_7$ is the terminal amino group of a peptidyl residue containing from 1 to 3 aminoacids;

d) a —$COR_a$ or $COR_8$ group in which $R_a$ is the terminal amino group of a peptidyl residue containing from 1 to 3 aminoacids and $R_8$ is $C_1$–$C_4$ alkoxy unsubstituted or substituted by phenyl or $R_8$ is a —$(CH_2)_n$—$NH_2$, —$(CH_2)_n$—$NR_4R_5$ or —$(CH_2)_n$—$NHR_6$ group in which n is 1 or 2 and $R_4$, $R_5$ and $R_6$ are as defined above;

e) a —Y—CO—Y'—$R_9$ group wherein each of Y and Y' which may be the same or different is —NH— or —O— and $R_9$ is phenyl or $C_1$–$C_6$ alkyl unsubstituted or substituted by phenyl; and f) a —$NHR_6$ or —$NHR_{10}$ group in which $R_6$ is as defined above and $R_{10}$ is $C_1$–$C_6$ alkyl substituted by 1 to 3 hydroxy groups;

and the others R, $R_1$, $R_2$ and $R_3$ are independently chosen from hydrogen, halogen, amino, hydroxy, $C_1$–$C_6$ alkyl, $C_1$–$C_6$ alkoxy, carboxy, $C_1$–$C_6$ alkoxy-carbonyl, $C_2$–$C_6$ alkanoyloxy, cyano and —$NR_4R_5$ in which $R_4$ and $R_5$ are as defined above, and the pharmaceutically acceptable salts of salt forming compounds of formula (I).

The invention includes within its scope all the possible isomers, stereoisomers, in particular Z- and E-isomers and their mixtures, and the metabolites and the metabolic precursors or bio-precursors (otherwise known as pro-drugs) of the compounds of formula (I).

A —$(CH_2)_m$— group may be a branched or straight $C_1$–$C_4$ alkylene chain, typically

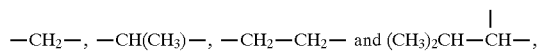

in particular —$CH_2$— and —$CH(CH_3)$—.

The alkyl groups, and the alkyl moiety in the alkanoyl groups, may be branched or straight alkyl chain. A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl.

A $C_1$–$C_6$ alkoxy group is, e.g., methoxy, ethoxy, propoxy, isopropoxy, butoxy or tert.butoxy, preferably methoxy, ethoxy or propoxy.

When $R_4$ and $R_5$ taken together with the nitrogen atom to which they are linked form a $C_4$–$C_7$ saturated heteromonocyclic ring, said ring can optionally contain a further heteroatom chosen from nitrogen, oxygen and sulphur. Typically said ring is a pyrrolidine, piperidine or morpholino ring.

Examples of aminoacids forming a peptidyl residue according to the meaning of $R_a$, $R_6$ and $R_7$ given above are alanine, glycine, histidine, threonine, glutamic acid, aspartic acid and tyrosine; preferably glycine, alanine and glutamic acid.

Accordingly, the $R_6$ terminal carbonyl group and the relevant peptidyl residue together may form a peptidoyl radical selected, for instance, from the group including —CO—CH($CH_3$)—$NH_2$, —CO—CH($CH_3$)—NHCO—CH($CH_3$)—$NH_2$, —CO—CH($NH_z$)—CH(OH)$CH_3$ and —CO—CH($CH_3$)—NHCO—CH($NH_2$)—$CH_2$—$CH_2$—COOH, in which the terminal amino group may be either free or in a protected or alkylated form as stated above.

Similarly the $R_a$ or $R_7$ terminal amino group and the relevant peptidyl residue is, for instance, a group selected independently from —NH—CH($CH_3$)—COOH, —NH—$CH_2$—COOH, —NH—CH(COOH)CH(OH)$CH_3$, —NH—CH($CH_3$)CONH—CH($CH_3$)COOH, —NH—CH(COOH)$CH_2$—$CH_2$—COOH, —NH—CH(COOH)$CH_2$COOH and —NH— CH(COOH)$CH_2$-phenyl.

When $R_6$ is the terminal carbonyl group of a peptidyl residue as defined above in which the terminal amino group is in a protected form, said amino group may be protected in a conventional way as known from the chemistry of peptides. Typically by an amino protecting group chosen from benzyloxycarbonyl, p-methoxybenzyloxycarbonyl, t.butoxycarbonyl (Boc), biphenylylisopropyloxycarbonyl (BBoc), 9-fluorenylmethyloxycarbonyl (Fmoc), triphenylmethyl (Trityl), 0-nitrobenzenesulfenyl (Nps), trimethylsylylethoxycarbonyl, di-p-nitrophenylethoxycarbonyl and trichloroethoxycarbonyl (Troc), preferably said amino protecting group being chosen from butoxycarbonyl (Boc) and 9-fluorenylmethyloxycarbonyl (Fmoc).

When $R_8$ is $C_1$–$C_4$ alkoxy substituted by phenyl it is in particular benzyloxy or phenethyloxy.

A —$(CH_2)_n$— group may be, for instance, a —$CH_2$, —$CH_2$—$CH_2$— or —$CH(CH_3)$— group, preferably —$CH_2$— or —$CH(CH_3)$—.

When $R_9$ is $C_1$–$C_6$ alkyl substituted by phenyl it is preferably a phenyl-$C_1$–$C_4$ alkyl group, in particular benzyl or phenethyl.

A $C_1$–$C_6$ alkyl group substituted by 1 to 3 hydroxy groups is preferably $C_1$–$C_4$ alkyl substituted by 1 or 2 hydroxy groups, typically $HOCH_2$—$CH(OH)$—$CH_2$— or $HOCH_2$—$CH_2$—$CH_2$—.

A halogen atom is, for instance, fluorine, chlorine, bromine or iodine, preferably a fluorine, chlorine or bromine atom.

A $C_2$–$C_6$ alkanoyl group, or alkanoyl moiety in alkanoyloxy groups, is preferably a $C_2$–$C_4$ alkanoyl group, in particular acetyl, propionyl or butyryl.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium bases, or with organic bases, e.g. alkylamines, preferably triethyl-amine.

As stated above, the present invention also includes within its scope pharmaceutically acceptable bio-precursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I) in which
one of R, $R_1$, $R_2$ and $R_3$ is independently a substituent selected from a') —X—$(CH_2)_m$—$NH_2$, —X—$(CH_2)_m$—$NR_4R_5$ or —X—$(CH_2)_m$—$NHR_6$ in which X is oxygen or —NH—, m is 1 or 2, one of $R_4$ and $R_5$ is $C_1$–$C_4$ alkyl and the other is hydrogen or $C_1$–$C_4$ alkyl or $R_4$ and $R_5$ taken together with the nitrogen atom to which they are linked form a pyrrolidine or piperidine ring, and $R_6$ is $C_2$–$C_4$ alkanoyl or the terminal carbonyl group of a peptidyl residue containing 1 or 2 aminoacids;

b') —NHC(NH)$NH_2$ or —N=CH—$NR_4R_5$ in which one of $R_4$ and $R_5$ is $C_1$–$C_4$ alkyl and the other is hydrogen or $C_1$–$C_4$ alkyl;

c') —X—$(CH_2)_m$—$COR_7$ in which X is —O— or —NH—, m is 1 or 2, $R_7$ is hydroxy, $C_1$–$C_4$ alkoxy, amino or $R_7$ is the terminal amino group of a peptidyl residue containing 1 or 2 aminoacids;

d') a —$COR_a$ or —$COR_8$ group in which $R_a$ is as defined above and $R_8$ is $C_1$–$C_4$ alkoxy unsubstituted or substituted by phenyl or $R_8$ is —$(CH_2)_n$—$NH_2$ or —$(CH_2)_n$$NR_4R_5$ in which n is 1 or 2 and one of $R_4$ and $R_5$ is $C_1$–$C_4$ alkyl and the other is hydrogen or $C_1$–$C_4$ alkyl or $R_4$ and $R_5$ taken together with the nitrogen atom to which they are linked form a pyrrolidine or piperidine ring; and e') —$NHR_6$ or —$NHR_{10}$ in which $R_6$ is $C_2$–$C_4$ alkanoyl or the terminal carbonyl group of a peptidyl residue containing 1 or 2 aminoacids and $R_{10}$ is $C_1$–$C_4$ alkyl substituted by one or two hydroxy groups;

and the others are independently chosen from hydrogen, halogen, amino, hydroxy, $C_1$–$C_4$ alkyl, $C_1$–$C_4$ alkoxy, $C_2$–$C_4$ alkoxycarbonyl, $C_2$–$C_4$ alkanoyloxy, cyano $C_1$–$C_4$ alkylamino or di($C_1$–$C_4$ alkyl)-amino; and the pharmaceutically acceptable salts of salt forming compounds of formula (I).

Examples of specific compounds of the invention are the following compounds which, when appropriate, may be either Z- or E-diastereoisomers or Z,E-mixtures of said diastereoisomers:

5-aminomethylcarbonyl-3-(indol-3-yl-methylene)-2-indolinone;

3-(indol-3-ylmethylene)-5-(2-piperidin-1-yl-acetyl)-2-indolinone (internal code FCE 28484);

5-(2,3-dihydroxy-propylamino)-3-(5-methoxy-indol-3-yl methylene)-2-indolinone (internal code FCE 28524);

3-(5-dimethylaminomethyleneamino-indol-2-ylmethylene)-2-indolinone (internal code FCE 28732);

N-[3-(5-bromo-2-indolinone-3-ylidenemethyl)-indol-5-yl] guanidine (internal code FCE 28885);

6-L-alanylamino-[3-(5-methoxy-indol-3-ylmethylene)-2-indolinone] (internal code FCE 28934);

5-alanylamino-3-[(5'-methoxy-3'-indolyl)methylene]-2-indolinone (internal code FCE 28901);

5-L-glutamyl-L-alanylamino-3-[(5'-methoxy-3'-indolyl) methylene]-2-indolinone (internal code FCE 28437);

and the pharmaceutically acceptable salts of salt forming members of the group.

The compounds of the invention, and the pharmaceutically acceptable salts thereof, can be obtained, for instance, by a process comprising:

a) reacting an aldehyde of formula (II)

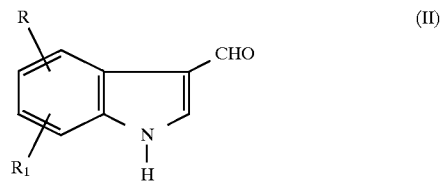

wherein R and $R_1$ are as defined above, with a compound of formula (III)

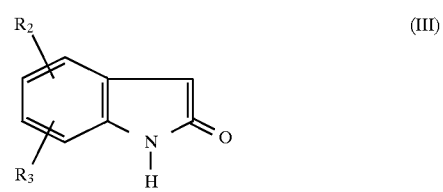

wherein $R_2$ and $R_3$ are as defined above; or b) reacting a compound of formula (IV)

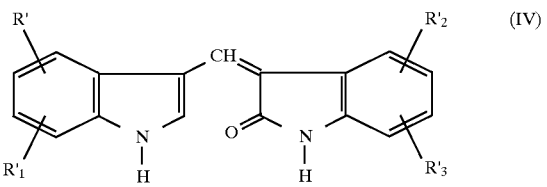

wherein
one or two of R', R'$_1$, R'$_2$ and R'$_3$ are —OH, —NH$_2$ or —SH and the others are as R, R$_1$, R$_2$ and R$_3$ as defined above, with an alkylating agent of formula (V) selected from

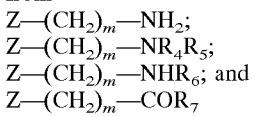

Z—(CH$_2$)$_m$—NH$_2$;
Z—(CH$_2$)$_m$—NR$_4$R$_5$;
Z—(CH$_2$)$_m$—NHR$_6$; and
Z—(CH$_2$)$_m$—COR$_7$ in which Z is a halogen atom and m, R$_4$, R$_5$, R$_6$ and R$_7$ are as defined above, thus obtaining a compound of formula (I) wherein one or two of R, R$_1$, R$_2$ and R$_3$ are as defined above under a) or c); or c) reacting a compound of formula (VI)

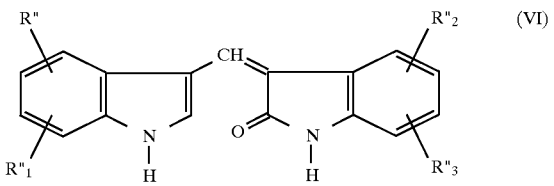

wherein
one or two of R'', R''$_1$, R''$_2$ and R''$_3$ are —OH or —NH$_2$ and the others are as R, R$_1$, R$_2$ and R$_3$ as defined above, with an acylating agent of formula (VII) selected from
HOOC—Y'—R$_9$;
HOOC—R$_a$;
HOOC—R$_8$;

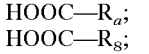

or a reactive carbonyl derivative thereof, wherein R$_a$, R$_8$, Y' and R$_9$ are as defined above, thus obtaining a compound of formula (I) wherein one or two of R, R$_1$, R$_2$ and R$_3$ are as defined above under d) or e); and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers.

The reaction of a compound of formula (II) with a compound of formula (III) is an analogy process which can be carried out according to known methods, as herebelow described; preferably in the presence of a basic catalyst, e.g. pyridine, piperidine, dimethylamine, or a suitable alkali metal hydroxide or alkoxide.

For example the reaction of a compound of formula (II) with a compound of formula (III) may be carried out under the conditions of the Knoevenagel reactions as described, e.g., by G. Jones in Organic Reactions 15, 204 (1967). Suitable catalysts are organic bases such as pyridine, piperidine or diethylamine.

The condensation may be performed in an inert organic solvent, e.g. pyridine, ethanol, methanol, benzene or dioxane at temperatures ranging from about 0° C. to about 100° C. Preferably the reaction is carried out in warm ethanol solution in the presence of piperidine catalyst.

In a compound of formula (V) the halogen atom Z is, for instance, iodine or bromine or chlorine, preferably bromine.

Alkylation of a compound of formula (IV) can be carried out according to known methods, for instance by reaction with sodium hydride and the bromide of a compound of formula (V) in a high boiling aromatic solvent such as xylene.

A reactive derivative of a carboxylic acid of formula (VII) is, for instance, a halide, e.g. an acyl chloride or an anhydride, typically a mixed anhydride or an in situ generated activated form from the carboxylic acid and a coupling reagent such as benzotriazole-1-yl-oxy-trispyrrolidinophosphonium hexafluorophosphate (PyBOP). Acylation reaction of a compound of formula (VI) with a compound of formula (VII) is preferably carried out in the presence of a basic agent such as pyridine, at a temperature ranging from about 0° C. to about 50° C.

A compound of formula (I) can be converted into another compound of formula (I) according to known methods. For instance, a compound of formula (I) in which one or two of R, R$_1$, R$_2$ and R$_3$ are carboxy and the others are as defined above can be converted into a corresponding compound of formula (I) wherein one or two of R, R$_1$, R$_2$ and R$_3$ are a group —COR$_a$ in which R$_a$ is as defined above, by acylation reaction with a suitable aminoacid or peptide in an organic solvent, e.g. CH$_2$Cl$_2$, in the presence of a basic agent such as pyridine or N-methylmorpholine.

A compound of formula (I) wherein one or two of R, R$_1$, R$_2$ and R$_3$ are an amino group and the others are as defined above can be converted into another compound of formula (I) in which one or two of R, R$_1$, R$_2$ and R$_3$ are a group —NHR$_{10}$ in which R$_{10}$ is as defined above, by a two-steps process. Accordingly, for instance, an amino group is reacted with 3-formyl-2,2-dimethyl-1,3-dioxolane followed by treatment with a reducing agent such as NaBH$_3$CN, thus converting the amino group into a 2,3-isopropylidene-dioxypropylamino group, which in its turn is treated with trifluoroacetic acid to obtain a —NHR$_{10}$ group wherein R$_{10}$ is 2,3-dihydroxypropyl.

A compound of formula (I) wherein one or two of R, R$_1$, R$_2$ and R$_3$ are amino and the others are as defined above can be converted into another compound of formula (I) in which one or two of R, R$_1$, R$_2$ and R$_3$ are —NHC(NH)NH$_2$, for instance by reaction with di(tert.butoxycarbonyl)thiourea (+O—CONHCSNHCOO+) according to known methods. The guanidino substituted compound thus obtained can in its turn be converted into another compound of formula (I) in which one or two of R, R$_1$, R$_2$ and R$_3$ are a group —NHC(NH)NR$_4$R$_5$ or —NHC(NH)CR$_6$ in which one or two of R$_4$ and R$_5$ are C$_1$–C$_6$ alkyl and R$_6$ is as defined above according to well known alkylation or acylation methods, respectively. Similarly a compound of formula (I) wherein one or two of R, R$_1$, R$_2$ and R$_3$ are amino and the others are as defined above can be converted, according to known methods, into another compound of formula (I) wherein one or two of R, R$_1$, R$_2$ and R$_3$ are a —N═CHNR$_4$R$_5$ group.

For instance, an amino substituted compound can be reacted with a suitable di(C$_1$–C$_6$ alkyl)N—CHO aldehyde in a suitable polar solvent, e.g. a lower alkanol, typically methanol or ethanol, in the presence of a basic agent, such as piperidine, to obtain a —N═CHNR$_4$R$_5$ compound in which R$_4$ and R$_5$ are C$_1$–C$_6$ alkyl.

The optional salification of a compound of formula (I) as well as the conversion of a salt into the free compound and the separation of a mixture of isomers into the single isomers may be carried out by conventional methods.

For example, the separation of a mixture of geometric isomers, e.g. cis- and trans-isomers, may be carried out by fractional crystallization from a suitable solvent or by chromatography, either column chromatography or high pressure liquid chromatography.

The intermediate compounds of formula (II) and (III) can be obtained according to known methods from known compounds, for instance as described in WO 91/13055 and WO 93/01182. The people skilled in the art will appreciate that the intermediate compounds of formulae (II) and (III) can be submitted to the same substituent chemical modifications as described in connection with the compounds of formula (I).

However, these substituent modifications can be properly performed at different levels within the process on the base of convenience depending on the nature of the substituents and on the compatibility of the transformations with the involved chemical structures. The intermediate compounds of formula (IV), (V), (VI) and (VII) are known compounds or can be obtained from known compounds. For instance, most of the compounds of formula (IV) and (VI) are known from WO 91/13055 and WO 93/01182 or can be similarly obtained.

Compounds of formula (III) (oxindole derivative), if not available, can also be obtained from the corresponding indole derivative by an analogy process through known methods. A preferred one is an oxidation-reduction process comprising the use of pyridinium bromide perbromide using a tertiary alcohol as solvent, preferably ter.butanol, followed by a reductive treatment with zinc in acetic acid or hydrogenation in the presence at palladium on charcoal.

When in the new compounds of the present invention and in the intermediate products used for their preparation there are groups present which need to be protected before the above-described reactions are performed, they may be protected before the reaction takes place and then deprotected at the end of the reaction according to well known methods in organic chemistry.

PHARMACOLOGY

The compounds of the invention possess specific tyrosine kinase inhibiting activity. It is believed that tyrosine kinase inhibitors may be of great importance in the control of uncontrolled cellular reproduction, i.e. in cellular reproduction disorders.

Recent studies on the molecular basis or neoplastic transformation have identified a family of genes, designated oncogenes, whose aberrant expression causes tumorigenesis. For example, the RNA tumour viruses possess such an oncogene sequence whose expression determines neoplastic conversion of infected cells. Several of their oncogene-encoded proteins, such as $pp60^{v\text{-}src}$, $p70^{gag\text{-}yes}$, $p130^{gag\text{-}fps}$ and $p70^{gag\text{-}fgr}$ display protein tyrosine kinase activity, that is they catalyze the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity.

Binding of the growth factor (GF) activates the receptors tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either over-produced and/or display altered substrate specificity may cause loss of growth control and/or neoplastic transformation. Accordingly, a specific inhibitor of tyrosine kinase can be useful in investigating the mechanism of cancerogenesis, cell proliferation and differentiations and it can be effective in prevention and chemotherapy of cancer and other pathological proliferative conditions. Hence the compounds according to the present invention can be useful in the treatment of pathological proliferation disorders in mammals, including humans. A human or animal, e.g. a mammal, can thus be treated by a method comprising the administration thereto of a therapeutically effective amount of one of the compounds of the invention. In this way the condition of the human or animal may be improved. Amelioration of the disease state or disorder from which the human or animal is suffering can be achieved. Typical examples of such disorders are benign and malignant tumors, including leukaemia such as myeloblastic leukaemia, lymphoma, sarcoma, neuroblastoma, Wilm's tumour, malignant neoplasm of the bladder, breast, lung or thyroid, neoplasias of epithelial origin, such as mammacarcinoma. Moreover, they can be useful in the treatment of epidermal hyperproliferation, such as psoriasis. The compounds of the invention can also be useful in inhibiting the development of the atheromatous plaque and restenosis, in the control of angiogenesis, as anti-metastatic agents and in treating diabetic complications. They have also utility as immunomodulating agents in the control of immune system diseases, e.g. as immunosuppressants, and in the treatment of Alzheimer's disease, as far as protein tyrosine kinases are involved in these diseases.

The tyrosine specific protein kinase activity of the compounds of the invention is shown, e.g., by the fact that they are active in the in vitro and in vivo test described herebelow.

In-vitro Assay p45 v-abl Kinase Purification

The enzyme used in our test was the p45 v-abl tyrosine kinase which represents the catalytic domain of the Abelson tyrosine kinase (isolated from the Abelson murine leukaemia virus). The p45 v-abl kinase was produced and isolated as described by Wang et al. in J. Biol. Chem. 260, 64 (1985) and by Ferguson et al. in J. Biol. Chem. 260, 3652 (1985) and in Biochem. J. 257, 321 (1989).

p45 v-abl Kinase Assay (Val$^5$)-Angiotension II phosphorylation was performed by incubation with 40 ng of purified abl-kinase and ($\gamma$-$^{32}$p)-ATP, in 50 μl of buffer containing Tris-HCl 25 mM, pH 8.0, MgCl$_2$ 10 mM and dithiothreitol 0.1 mM (kinase buffer). The reaction mixture was incubated for the indicated time at 30° C. and the reaction stopped by adding 50 μl of 5% trichloroacetic acid. After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. IC$_{50}$ values were calculated from triplicated determinations of each experimental point. Each inhibitor was tested at concentrations ranging from 0 to 400 μg in the presence of fixed concentrations of peptide (2 Mm) and ATP (50 μM).

In-vivo Assay

K562 Cell Growth Inhibition Assay

K562 cells, a human myelogenous leukemia cell line, were seeded into a 24 wells tissue culture plate (Falcon 3047) (10000/well) in the presence of increasing concentrations of the compounds. After 72 h, cells were harvested and were counted using a cell counter (Coulter Counter-ZM). The percent of inhibition was evaluated in respect to the untreated control cells.

The inhibitory activity data for a representative group of compounds according to the present invention, obtained both in the in-vitro p45 v-abl kinase assay and in the in-vivo human chronic myeloid leukemia K562 cell growth inhibition assay described above, are set out in following Table 1.

TABLE 1

Inhibition of p45 kinase and K562 cell growth

| Compound | IC$_{50}$ ($\mu$M) | |
|---|---|---|
| | v-abl | K562 |
| FCE 28484 | 0.78 | 4.82 |
| FCE 28437 | 0.5 | 14.75 | where
FCE 28484 means 3-(indol-3-ylmethylene)-5-(2-piperidin-1-yl-acetyl)-2-indolinone; and
FCE 28437 means 5-L-glutamyl-L-alanylamino-3-[(5'-methoxy-3'-indolyl)methylene]-2-indolinone.

In view of their high activity, the compounds of the invention can be used in medicine in treating a patient in need of tyrosine kinase inhibition.

The compounds of the invention can be administered in a variety of dosage forms, e.g. orally, in the form of tablets, capsules, sugar- or film-coated tablets, liquid solutions or suspensions; rectally, in the form of suppositories; parenterally, e.g. intramuscularly, or by intravenous injection of infusion; or topically. The dosage depends on the age, weight, condition of the patient and administration route. For example, the dosage adopted for oral administration to adult humans for the compound FCE 28484 may range from about 10 to about 150–200 mg per dose, from 1 to 5 times daily. Of course, these dosage regimens may be adjusted to provide the optimal therapeutic response.

The invention includes pharmaceutical compositions comprising a compound of formula (I) or a pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating or film-coating processes.

The liquid dispersion for oral administration may be, e.g., syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin. Compositions for topical application, e.g. creams, lotions or pastes, can be prepared by admixing the active ingredient with a conventional oleaginous or emulsifying excipient.

A further object of the present invention is a combined method of treatment of cancer or of amelioration of the conditions of mammals, including humans, suffering from cancer, said method comprising administering 1) a compound of the invention, or a pharmaceutically acceptable salt thereof, and 2) an additional antitumor agent, in amounts and close enough together in time sufficient to produce a therapeutically useful effect.

The present invention also provides products containing a compound of the invention, or a pharmaceutically acceptable salt thereof, and an additional antitumor agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice.

Examples of antitumor agents that can be formulated with a compound of the invention or, alternatively, can be administered in a combined method of treatment, include doxorubicin, daunomycin, epirubicin, idarubicin, 4'-iododoxorubicin, methoxy-morphlino-doxorubicin, etoposide, fluorouracil, melphalan, cyclophosphamide, bleomycin, vinblastin and mitomycin or a mixture of two or more thereof.

The compounds of the invention can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above, together with the antitumor agent.

A compound of the invention and an antitumor agent such as an anthracycline glycoside can be administered to improve the condition of a patient having a leukaemia such as myeloblastic leukaemia, lymphoma, sarcoma, neuroblastoma, Wilm's tumour or malignant neoplasm of the bladder, breast, lung or thyroid.

The following examples illustrate but do not limit the invention.

EXAMPLE 1

Preparation of FCE 28484

To a suspension of aluminum chloride anhydrous (11.4 g, 85 mmole) in 1,2-dichloroethane (10 ml) was added dropwise bromoacetyl bromide (5.9 ml, 68 mmole) with stirring at 0° C.

After the stirring was continued 1 h, 2-indolinone (4.52 g, 34 mmole) dissolved in 1,2-dichloroethane (10 ml) was added, the mixture was stirred 2 h at 0° C. and then heated 3 h at 50° C.

The reaction mixture was poured into ice and water (500 ml) and filtered to give 5-(2-bromoacetyl)-2-indolinone (7.5 g).

A solution of piperidine (0.39 ml, 3.9 mmole) and 5-(2-bromoacetyl)-2-indolinone (500 mg, 1.97 mmole) in N,N-dimethylformamide (15 ml) was stirred at room temperature 4 h then was poured into water (50 ml) and washed with dichloromethane (250 ml), the organic solution was washed with water several times and dried over sodium sulfate. After evaporation of the solvent the residue was chromatographed on silica-gel using ethyl acetate as eluant to give 5-(2-piperidin-1-yl-acetyl)-2-indolinone (250 mg).

To a solution of indole-3-carboxaldehyde (150 mg, 1.03 mmole) and 5-(2-piperidin-1-yl-acetyl)-2-indolinone (250 mg, 0.97 mmole) in ethanol (10 ml) piperidine (0.15 ml, 1.5 mmole) was added with stirring at 80° C.

After the stirring was continued 3 h the mixture gave a solid that was filtered and washed with ethanol to give 3-(indol-3-ylmethylene)-5-(2-piperidin-1-yl-acetyl)-2-indolinone (FCE 28484) (250 mg).

$^1$H NMR (400 MHz, DMSO, δ ppm) 1.3–1.6 (m, 6H); 2.50 (m, 4H); 3.78 (s, 2H); 6.93 (d, J=7.9 Hz, 1H); 7.25 (m, 2H); 7.53 (m, 1H); 7.86 (dd, J=1.7 Hz, J=8.2 Hz, 1H); 8.22 (m, 1H); 8.29 (s, 1H); 8.50 (d, J=1.7 Hz, 1H); 9.45 (s, 1H); 10.8 (bs, 1H); 12.0 (bs, 1H).

FD-MS: m/z 386 (39 [MH]$^+$); 385 (33 [M]$^+$); 98 (100 [C$_6$H$_{12}$])$^+$)

By proceeding analogously, with proper modification introducing the amino group by using the Gabriel synthesis, the following compound can be obtained: 5-aminomethylcarbonyl-3-(indol-3-yl-methylene)-2-indolinone.

EXAMPLE 2
Preparation of FCE 28524

To a solution of 5-methoxy-indole-3-carbaldehyde (175 mg, 1 mmole) and 5-terbutoxycarbonylamino-2-indolinone (250 mg, 1 mmole) in ethanol (20 ml) piperidine (0.1 ml, 1 mmole) was added with stirring at 80° C.

After the stirring was continued 8 h the mixture gave a solid that was filtered and washed with ethanol to give 3-(5-methoxy-indol-3-yl-methylene)-5-terbutoxycarbonyl-amino-2-indolinone (255 mg).

The solid was taken up with dichloromethane (10 ml) and trifluoroacetic acid (2 ml) was added with stirring at room temperature.

After 1 h dichloromethane (50 ml) was added and the mixture was washed with water and made alkaline with 2N sodium hydroxide and then washed several times with water and dried over sodium sulfate and concentrated under reduced pressure, the solution after standing overnight at 4° C. gave crystals that were filtered and washed with cold dichloromethane to obtain 3-(5-methoxy-indol-3-yl-methylene)-5-amino-2-indolinone (200 mg).

To a solution of 3-(5-methoxy-indol-3-yl-methylene)-5-amino-2-indolinone (200 mg, 0.65 mmole), 2,2-dimethyl-[1,3]dioxolane-4-carbaldehyde (170 mg, 1.3 mmole) and 1N hydrochloric acid (1 ml) in methanol (10 ml) sodium cyanoborohydride (220 mg, 3.25 mmole) was added with stirring at room temperature.

After the stirring was continued 4 h, the reaction mixture was diluted with dichloromethane (100 ml) and washed several times with water.

The organic layer was dried over sodium sulfate and concentrated under reduced pressure, the residue was chromatographed on silica-gel using a mixture of ethyl acetate and methanol (9:1) as eluant to give 5-[(2,2-dimethyl-[1,3]dioxolan-4-yl-methyl)-amino]-3-(5-methoxy-indol-3-ylmethylene)-2-indolinone (120 mg).

To a solution of 5-[(2,2-dimethyl-[1,3]dioxolan-4-yl-methyl)-amino]-(5-methoxy-indol-3-ylmethylene)-2-indolinone (120 mg, 0.28 mmole) in dichloromethane (15 ml) trifluoroacetic acid (1 ml) was added with stirring at 0° C.

After the stirring was continued 1 h the solution was diluted with dichloromethane (100 ml) and washed with saturated sodium bicarbonate and then with water.

The organic layer was dried over sodium sulfate and concentrated under reduced pressure, the residue was chromatographed on silica-gel using a mixture of ethyl acetate and methanol (9:1) as eluant to give 5-(2,3-dihydroxy-propylamino)-3-(5-methoxy-indol-3-yl methylene)-2-indolinone (FCE 28524) (50 mg).

$^1$H NMR (400 MHz, DMSO, δ ppm) 2.7–3.3 (m, 2H$_{E+Z}$); 3.5–3.8 (m, 1H$_{E+Z}$); 3.80–3.86 (two singlets, 3H$_{E+Z}$); 4.4–5.2 (bs, 3H$_{E+Z}$); 6.45 (m, 1H$_{E+Z}$); 6.58–6.62 (two doublets, J=6.8 Hz, J=6.8 Hz, 1H$_{E+Z}$); 6.85 (m, 1H$_{E+Z}$); 7.13 (d, J=2.2 Hz, 1H$_E$); 7.18 (d, J=2.2 Hz, 1H$_Z$); 7.23 (d, J=2.2 Hz, 1H$_E$); 7.40 (two doublets, J=8.7 Hz, J=8.8 Hz, 1H$_{E+Z}$); 7.62 (d, J=2.6 Hz, 1H$_Z$); 7.76 (s, 1H$_E$); 7.94 (s, 1H$_Z$); 8.17 (s, 1H$_E$); 9.38 (s, 1H$_Z$); 10.00–10.05 (two singlets, 1H$_{E+Z}$); 11.7–12.1 (bs, 1H$_{E+Z}$).

FD-MS: m/z 379 (100 [M]$^+$); 306 (26 [M-CH$_2$CHOHCH$_2$OH+2H]$^+$)

EXAMPLE 3
Preparation of FCE 28732

A solution of 5-aminoindole (5 g, 37.87 mmole), triethylamine (10.6 ml, 76.5 mmole) and diterbutylpyrocarbonate (8.35 g, 38.25 mmole) in dioxane (150 ml) was stirred at room temperature 4 h.

The solution was concentrated under reduced pressure and the residue was taken up with dichloromethane (150 ml) and washed with water.

The organic layer was dried over sodium sulfate and concentrated under reduced pressure, the residue was chromatographed on silica-gel using a mixture of cyclohexane and ethyl acetate (7:3) as eluant to give 5-terbutoxycarbonylamino-indole (8.7 g).

A solution of 5-terbutoxycarbonylamino-indole (8.7 g, 37.5 mmole) in acetic anhydride (20 ml) was added dropwise in about 30 min in a solution of imidazole (2.65 g, 39 mmole) in acetic anhydride (20 ml) at 125° C.

After stirring 1 h the mixture was concentrated under reduced pressure and the residue was crystallized with acetonitrile, the solid was filtered and taken up with ethanol (100 ml) and water (50 ml), sodium hydroxide (5 g) was added.

After stirring 1 h at reflux the solution was diluted with water (1 l) and made neutral with 1N hydrochloric acid, then after standing overnight at 4° C. gave 5-terbutoxycarbonylamino-indole-3-carbaldehyde (5.7 g).

To a solution of 5-terbutoxycarbonylamino-indole-3-carbaldehyde (200 mg, 0.77 mmole) and 2-indolinone (100 mg, 0.75 mmole) in ethanol (15 ml) piperidine (0.06 ml, 0.6 mmole) was added at 60° C. with stirring.

After stirring 4 h at 60° C. the reaction mixture was diluted with dichloromethane (50 ml) and washed with water, the organic layer was dried over sodium sulfate and concentrated under reduced pressure, the residue was taken up with trifluoroacetic acid (5 ml) and stirred 1 h at 0° C.

After stirring at room temperature 1 h the mixture was diluted with dichloromethane (100 ml) and washed with 2N sodium hydroxide and then with brine.

The organic layer was dried over sodium sulfate and concentrated under reduced pressure.

The residue was taken up with tetrahydrofuran (25 ml) and triethylamine (1.9 ml, 13.3 mmole), chlorodimethyl-formiminium chloride (1.6 g, 12.6 mmole) was added portionwise at 0° C.

After the stirring was continued 1 h at room temperature, the reaction mixture was diluted with dichloromethane (150 ml) and washed with saturated sodium bicarbonate and then with brine, the organic layer was dried over sodium sulfate and concentrated under reduced pressure, the residue was chromatographed on silica-gel with a mixture of ethyl acetate and methanol (1:1) as eluant to give 3-(5-dimethylaminomethyleneamino-indol-2-ylmethylene)-2-indolinone (FCE 28732) (110 mg).

$^1$H NMR (400 MHz, DMSO, δ ppm) 2.98 (bs, 6H$_{E+Z}$); 6.85 (m, 2H$_{E+Z}$); 6.95 (m, 1H$_{E+Z}$); 7.04 (d, J=2.0 Hz, 1H$_E$); 7.10 (m, 1H$_Z$); 7.17 (m, 1H$_E$); 7.33 (d, J=8.2 Hz, 1H$_Z$); 7.37 (d, J=8.5, Hz, 1H$_E$); 7.64 (d, J=2.0 Hz, 1H$_Z$); 7.74 (m, 2H$_E$); 7.79 (s, 1H$_Z$); 7.86 (s, 1H$_E$); 7.88 (d, J=7.5 Hz, 1H$_Z$); 8.10 (s, 1H$_Z$); 8.13 (s, 1H$_E$); 9.35 (s, 1H$_Z$); 10.47 (bs, 1H$_{E+Z}$); 11.9 (bs, 1H$_{E+Z}$).

FD-MS: m/z 330 (100 [M]$^+$)

EXAMPLE 4
Preparation of FCE 28885

To a solution of 5-terbutoxycarbonylamino-indole-3-carbaldehyde (50 mg, 0.19 mmole) and 5-bromo-2-indolinone (40 mg, 0.19 mmole) in ethanol (5 ml) piperidine (0.02 ml, 0.2 mmole) was added with stirring at 80° C.

After the stirring was continued 4 h at 80° C. the mixture gave a solid which after filtration and washing with ethanol gave 3-(5-terbutoxycarbonylamino-indol-3-ylmethylene)-5-bromo-2-indolinone (70 mg).

The solid was taken up with trifluoroacetic acid (5 ml) and after stirring at room temperature for 1 h the mixture was diluted with ethyl acetate (100 ml) and washed with 1N sodium hydroxide and brine.

The organic layer was concentrated under reduced pressure, the residue was dissolved in N,N-dimethylformamide (15 ml) and triethylamine (0.03 ml, 0.2 mmole), bis-terbutoxycarbonylthyourea (60 mg, 0.2 mmole), HgCl$_2$ (80 mg, 0.2 mmole) were added with stirring.

After stirring 1 h at room temperature the mixture was filtered on a pad of celite and washed with ethyl acetate.

The solution was washed with water several times and the organic layer was dried on sodium sulfate and concentrated under reduced pressure.

The residue was chromatographed on silica-gel with a mixture of ethyl acetate and cyclohexane (2:1) as eluant to give N-[3-(5-bromo-2-indolinone-3-ylidenemethyl)-indol-N',N"diterbutoxycarbonyl-guanidine (30 mg, 0.05 mmole).

The solid was taken up with trifluoroacetic acid (5 ml) with stirring at room temperature.

The mixture was diluted with ethyl acetate (50 ml) and washed with 1N sodium hydroxide and then with brine. The organic layer was dried on sodium sulfate and concentrated under reduced pressure, the residue was chromatographed on Lo-Bar RP-18 column with water as eluant to give N-[3-(5-bromo-2-indolinone-3-ylidene-methyl)-indol-5-yl] guanidine (FCE 28885) (8 mg) after freeze-drying.

$^1$H NMR (400 MHz, DMSO, δ ppm) 6.79 (d, J=8.4 Hz, 1H$_Z$); 6.85 (d, J=8.4 Hz, 1H$_E$); 7.10 (m, 1H$_{E+Z}$); 7.27 (dd, J=1.8 Hz, J=8.4 Hz, 1H$_Z$); 7.37 (dd, J=1.8 Hz, J=8.4 Hz, 1H$_E$); 7.58 (m, 2H$_{E+Z}$); 7.83 (d, J=1.8 Hz, 1H$_E$); 7.90 (s, 1H$_E$); 8.20 (d, J=1.8 Hz, 1H$_Z$); 8.24 (d, J=1.8 Hz, 1H$_Z$); 8.27 (s, 1H$_Z$); 8.34 (s, 1H$_E$); 9.51 (s, 1H$_Z$); 10.64 (two singlets, 1H$_{E+Z}$); 12.2 (bs, 1H$_{E+Z}$).

FAB-MS: m/z 434 (27 [M+K]$^+$); 396 (100 [M+H]$^+$)

EXAMPLE 5
Preparation of FCE 28934

To a solution of 6-nitroindole (1.62 g, 10 mmole) in terbutanol (100 ml) pyridine hydrobromide perbromide (9.6 g, 30 mmole) was added portionwise in 30 min with stirring.

After the stirring was continued 1 h at room temperature the solvent was removed under reduced pressure and the residue taken up with ethyl acetate (250 ml) and washed with water. The organic layer was dried over sodium sulfate and concentrated under reduced pressure.

The residue was dissolved in acetic acid (50 ml) and zinc dust (4.3 g, 65 mmole) was added with stirring at 0° C. After 1 h the mixture was filtered on a pad of celite and washed with ethyl acetate (250 ml).

The organic layer was washed with 5% sodium bicarbonate and then with brine, the solvent was removed under reduced pressure.

The residue was dissolved in dioxane (50 ml), triethylamine (0.8 ml, 5.6 mmole) and diterbutylpyrocarbonate (1.2 g, 5.5 mmole) were added with stirring. After stirring 2 h at room temperature the mixture was diluted with ethyl acetate (100 ml) and washed with water. The organic layer was dried on sodium sulfate and concentrated under reduced pressure.

The residue was chromatographed on silica-gel with a mixture of ethyl acetate and cyclohexane (1:1) as eluant to give 6-terbutoxycarbonylamino-2-indolinone (100 mg).

FD-MS: m/z 248 (100 [M]$^+$)

To a solution of 6-terbutoxycarbonylamino-2-indolinone (40 mg, 0.16 mmole) and 5-methoxy-indole-3-carbaldehyde (30 mg, 0.16 mmole) in ethanol (5 ml), piperidine (0.01 ml, 0.1 mmole) was added with stirring at 80° C.

After stirring was continued 4 h at 80° C. the solvent was removed under reduced pressure and the residue was chromatographed on silica-gel with a mixture of ethyl acetate and cyclohexane (1:1) as eluant to give 6-terbutoxycarbonylamino-3-(5-methoxy-indol-3-ylmethylene)-2-indolinone (75 mg, 0.18 mmole).

The solid was taken up with trifluoroacetic acid (5 ml) and stirred at room temperature 15 min.

The reaction mixture was diluted with ethyl acetate (50 ml) and washed with 5% sodium bicarbonate, the organic layer was dried over sodium sulfate and concentrated under reduced pressure.

The residue was dissolved in tetrahydrofuran (10 ml) and fluorenylmethoxycarbonyl-L-alanine (75 mg, 0.24 mmole), benzotriazol-1-yl-oxy-tripyrrolidinophosphonium-hexafluorophosphate (130 mg, 0.25 mmole) were added with stirring.

After the stirring was continued 1 h at room temperature the mixture was diluted with ethyl acetate (50 ml) and washed with brine.

The organic layer was dried over sodium sulfate and concentrated under reduced pressure.

The residue was taken up with ethyl acetate (50 ml) and piperidine (1 ml) was added with stirring at room temperature.

After stirring 3 h the solvent was removed under reduced pressure, at the residue was added water (5 ml), 1N hydrocloric acid was added dropwise until all the solid was dissolved, the solution was chromatographed on LoBar RP18 column with water as eluant to give 6-L-alanylamino-[3-(5-methoxy-indol-3-ylmethylene)-2-indolinone] (FCE 28934) (10 mg).

$^1$H NMR (400 MHz, DMSO, δ ppm) 1.36 (d, J=6.5 Hz, 3H$_Z$); 1.38 (d, J=6.5 Hz, 3H$_E$); 3.77 (s, 3H$_E$); 3.80 (m, 1H$_{E+Z}$); 3.86 (s, 3H$_Z$); 6.85 (m, 1H$_{E+Z}$); 7.10 (m, 2H$_E$+1H$_Z$); 7.40 (m, 2H$_{E+Z}$); 7.68 (m, 1H$_{E+Z}$); 7.76 (s, 1H$_E$); 7.84 (d, J=8.4 Hz, 1H$_Z$); 8.03 (s, 1H$_Z$); 8.12 (d, J=2.5 Hz, 1H$_E$); 9.33 (d, J=2.9 Hz, 1H$_Z$); 10.51 (s, 1H$_E$); 10.52 (s, 1H$_Z$); 11.8 (bs, 1H$_{E+Z}$).

FAB-MS: m/z 377 (100 [MH]$^+$); 306 (17 [MH—COCH(CH$_3$) NH$_2$+H]$^+$)

EXAMPLE 6

Preparation of FCE 28901

To a stirred solution of 5-nitroindole (4 g, 24.6 mmol) in 200 ml of t-Butanol was added, portionwise, pirydinium bromide perbromide (30 g, 93 mmol) over a period of 0.5 h. The reaction mixture was stirred at room temperature overnight, then t-Butanol was removed and the resulting residue dissolved in ethyl acetate/water (500/500 ml). The organic layer was separated and the aqueous layer was extracted with 300 ml of ethyl acetate. The organic extracts were washed with water, dried over sodium sulphate anhydrous and concentrated in vacuo to give 8.5 g of a less polar compound that was recrystallized from ethyl acetate to give 7.5 g of dibromoderivative. Hydrogenation of this compound with 10 equivalents of zinc dust in 80 ml of acetic acid at room temperature for 3 h gave 5-amino oxindole in good yields (3 g, 82% yield).

EI-MS: m/z 148 (100, $[M]^+$); 120 (56, $[M-CO]^+$); 119 (94, $[M-CO-H]^+$); 105 (22, $[M-HNCO]^+$)

To a solution of 5-amino oxindole (2 g, 13.5 mmol) in 80 ml of water/dioxane 3:1 was added sodium hydroxide 1N until obtaining pH 10 and then di-t-Butyl pyrocarbonate (3.5 g, 16.2 mmol). The reaction was stirred for 3 h maintaining pH 10. After extraction with 3×10 ml of ethyl acetate, the extracted were dried over sodium sulphate and evaporated obtaining 2.4 g of 5-t-Butoxycarbonylamino oxindole (71% yield).

$^1$H-NMR (400 MHz, DMSO, T=45° C.) 1.49 (s, 9H); 3.87 (s, 3H); 6.72 (d, J=8.4 Hz, 1H); 6.86 (dd, J=2.2 Hz, J=8.8 Hz, 1H); 7.12 (dd, J=1.8 Hz, J=8.4 Hz, 1H); 7.40 (d, J=8.8 Hz, 1H); 7.54 (d, J=2.2 Hz, 1H); 7.78 (d, J=1.8 Hz, 1H); 7.92 (s, 1H); 8.87 (bs, 1H); 9.38 (s, 1H); 10.25 (s, 1H); 11.8 (bs, 1H). FD-MS: 248 (100, $[M]^+$); 191 (18, $[M-C_4H_9]^+$); 147 (5, $[M-(CH_3)_3COCO]^+$)

To a solution of 5-t-Butoxycarbonylamino oxindole (630 mg, 2.5 mmol) and 5-methoxyindolcarboxaldehyde (450 mg, 2.6 mmol) in absolute ethanol was added piperidine (0.26 ml, 2.6 mmol). The reaction was carried out at 80° C. for 3 h. Ethanol was evaporated and the residue was purified by silica gel chromatography (eluents: cyclohexane/ethyl acetate 2:3) obtaining 800 mg of product that was solubilized in 10 ml of methylene chloride and, after addition of 40 ml of trifluoroacetic acid, was stirred for 1 h at room temperature. The solvent was evaporated and the residue was crystallized with diethyl ether obtaining 750 mg of 5-amino-3-[(5'-methoxy 3'-indolyl) methylene] 2-oxindole (90% yield).

$^1$H-NMR (400 MHz, DMSO) 3.87 (s, 3H); 6.87 (dd, J=2.4 Hz, J=8.5 Hz, 1H); 6.90 (d, J=8.2 Hz, 1H); 7.07 (dd, J=8, 2 Hz, J=2.0 Hz, 1H); 7.42 (d, J=8.5 Hz, 1H); 7.66 (d, J=2.4 Hz, 1H); 7.81 (d, J=2.0 Hz, 1H); 8.18 (s, 1H); 9.44 (d, J=3.1 Hz, 1H); 9.65 (bs, 3H); 10.67 (s, 1H); 12.03 (d, J=3.1 Hz, 1H).

FD-MS: m/z 306 (55, $[MH]^+$); 305 (100, $[M]^+$)

To a solution of 5-Amino-3-[(5'-methoxy-3'-indolyl) methylene]-2-oxindole (500 mg, 1.64 mmol) and of t-Butoxycarbonyl (L)-alanine in 80 ml of tetrahydrofuran were added (950 mg, 1.87 mmol) of benzotriazole 1-yloxy-tris pyrrolidino phosphonium hexafluorophosphate and (0.20 ml, 1.87 mmol) of N-Methylmorpholine. The reaction was carried out at room temperature for 4 h.

After evaporation of tetrahydrofuran, the residue was purified by flash chromatography (eluents: cyclohexane/ethyl acetate 3:7) then, it was solubilized in methylene chloride and, after stirring for 1 h with 10 ml of trifluoroacetic acid, 600 mg of 5-alanylamino-3-[(5'-methoxy-3'-indolyl)methylene]-2-indolinone (FCE 28901) were obtained (81% yield).

$^1$H-NMR (400 MHz, DMSO) 1.24 (d, J=6.5 Hz, 3H); 3.46 (m, 1H); 3.87 (s, 3H); 6.76 (d, J=8.2 Hz, 1H); 6.85 (dd, J=2.4 Hz, J=8.5 Hz, 1H); 7.40 (d, J=8.5 Hz, 1H); 7.48 (dd, J=2.1 Hz, J=8.2 Hz, 1H); 7.62 (d, J=2.4 Hz, 1H); 7.89 (d, J=2.1 Hz, 1H); 8.02 (s, 1H); 9.41 (s, 1H); 9.8 (bs, 1H); 10.43 (s, 1H); 11.9 (bs, 1H).

FD-MS: m/z 376 (100, $[M]^+$); 331 (46, $[M-CH_3CH_2NH_2)^+]$); 305 (24, $[M-COCH(CH_3)NH_2+H]^+$)

EXAMPLE 7

Preparation of FCE 28437

To a solution of 5-alanylamino-3-((5'-methoxy-3'-indolyl) methylene]-2-oxindole (600 mg, 1.42 mmol) and Boc-(L)-Glutamic acid (t-Butyl ester), (500 mg, 1.65 mmol) were added 930 mg (1.8 mmol) of benzotriazole-1-yloxy-tris pirrolidino phosphonium hexafluorophosphate and 0.20 ml (1.8 mmol) of N-Methylmorpholine. The reaction was stirred at room temperature for 3 h, then, after evaporation of tetrahydrofuran, the residue was purified by flash chromatography (eluent: ethyl acetate) obtaining 200 mg of product that was solubilized in 8 ml of methylene chloride and stirred for 1 h after addition of 8 ml of trifluoroacetic acid. The residue, solubilized in ethyl acetate, was precipitated by adding diethyl ether and purified on reversed phase (eluents: water/methanol 1:2) obtaining 100 mg of 5-L-glutamyl-L-alanylamino-3-[(5'-methoxy-3'-indolyl) methylene]-2-indolinone (FCE 28437) (51% yield)

$^1$H-NMR (400 MHz, DMSO) 1.30 (d, J=7.0 Hz, $3H_E$); 1.35 (d, J=7.0 Hz, $3H_Z$); 1.5–1.9 (m, $2H_{E+Z}$); 2.27 (m, $2H_{E+Z}$); 3.2–3.5 (m, $1H_{E+Z}$); 3.81 (s, $3H_Z$); 3.87 (s, $3H_Z$); 4.3–4.5 (m, $1H_{E+Z}$); 6.7–6.9 (m, $2H_{E+Z}$); 7.21 (d, J=2.6 Hz, $1H_E$); 7.25 (dd, J=1.8 Hz, J=8.4 Hz, $1H_E$); 7.31 (dd, J=1.8 Hz, J=8.4 Hz, 1H); 7.40 (m, $1H_{E+Z}$); 7.61 (d, J=2.6 Hz, $1H_Z$); 7.85 (s, $1H_E$); 7.89 (d, J=1.8 Hz, $1H_Z$); 8.00 (s, $1H_Z$); 8.19 (s, $1H_E$); 8.3 (bs, $1H_{E+Z}$); 8.5 (d, J=1.8 Hz, $1H_E$); 9.41 (s, $1H_Z$); 9.92 (s, $1H_Z$); 10.03 (s, $1H_E$); 10.35 (s, $1H_E$); 10.44 (s, $1H_Z$); 11.9 (bs, $1H_{E+Z}$).

FAB-MS: m/z 506 (61,$[M]^+$); 377 (43,$[MH-Glu]^+$); 306 (100, $[MH-GluAla]^+$).

EXAMPLE 8

To a suspension of 3-(indol-3-ylmethylene)-5-(2-piperidin-1-yl-acetyl)-2-indolinone (100 mg) in water (10 ml) the stoichiometric amount of 0,1N HCl solution (3 ml) was added. The solution was freeze-dried to give 105 mg of 3-(indol-3-ylmethylene)-5-(2-piperidin-1-yl-acetyl)-2-indolinone hydrochloride.

EXAMPLE 9

To a suspension of 3-(indol-3-ylmethylene)-5-(2-piperidin-1-yl-acetyl)-2-indolinone (25 mg) in water (10 ml) Amberlite Ira 900® (HCl form) was added until the solution turned clear. The resin was filtered and washed with water and the solution freeze-dried to give 3-(indol-3-ylmethylene)-5-(2-piperidin-1-yl-acetyl)-2-indolinone hydrochloride (20 mg).

EXAMPLE 10

Capsules, each dosed at 0.200 g and containing 20 mg of the active substance can be prepared. Composition for 500 capsules:

| | |
|---|---|
| 3-(indol-3-ylmethylene)-5-(2-piperidin-1-yl-acetyl)-2-indolinone | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

EXAMPLE 11

Tablets, each weighing 0.150 g and containing 25 mg of the active substance, can be manufactured as follows. Composition for 10,000 tablets:

| | |
|---|---|
| 3-(indol-3-ylmethylene)-5-(2-piperidin-1-yl-acetyl)-2-indolinone | 250 g |
| Lactose | 800 g |
| Corn starch | 415 g |
| Talc powder | 30 g |
| Magnesium stearate | 5 g |

The 3-(indol-3-yl methylene)-5-(2-piperidin-1-yl-acetyl)-2-indolinone, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 12

Intravenous infusion 1–10 mg/ml.

An intravenous infusion pharmaceutical preparation can be manufactured by dissolving 50 mg of 3-(indol-3-yl methylene)-5-(2-piperidin-1-yl-acetyl)-2-indolinone in water for injection (1000 ml) and sealing glass ampoules of 1–10 ml.

Prior to infusion, the obtained solution can be diluted according to the common practice, and stored and/or delivered in glass, polypropylene, polyolefin or polyethylene-lined equipment.

We claim:

1. Indol-3-ylmethylene-2-oxindole derivative having the following formula (I)

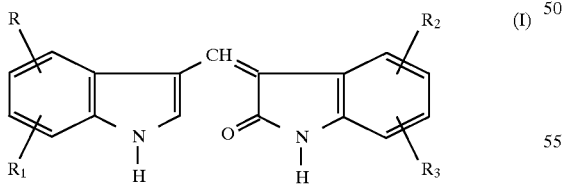

wherein
one or two of R, $R_1$, $R_2$ and $R_3$ are a substituent selected independently from:

a) a —X—$(CH_2)_m$—$NH_2$, —X—$(CH_2)_m$—$NR_4R_5$, or —X—$(CH_2)_m$—$NHR_6$ group, in which X is —O—, —S— or —NH—, m is an integer of 1 to 4, one of $R_4$ and $R_5$ is hydrogen or $C_1$–$C_6$ alkyl and the other is $C_1$–$C_6$ alkyl or $R_4$ and $R_5$ taken together with the nitrogen atom to which they are linked form a $C_4$–$C_7$ saturated heteromonocyclic ring, and $R_6$ is $C_2$–$C_6$ alkanoyl or the terminal carbonyl group of a peptidyl residue containing from 1 to 3 amino acids wherein the terminal amino group is either free or in a protected form or in an alkylated form to provide a —$NR_4R_5$ group in which $R_4$ and $R_5$ are as defined above;

b) a —NHC(NH)$NH_2$, —NHC(NH)$NR_4R_5$, —NHC(NH)$NHR_6$, —N=CH—$NH_2$, —N=CH—$NR_4R_5$ or —N=CH—$NHR_6$ group in which $R_4$, $R_5$ and $R_6$ are as defined above;

c) a —X—$(CH_2)_m$—$COR_7$ group wherein X and m are as defined above, $R_7$ is hydroxy, amino, $C_1$–$C_6$ alkoxy or —$NR_4R_5$ in which $R_4$ and $R_5$ are as defined above, or $R_7$ is the terminal amino group of a peptidyl residue containing from 1 to 3 aminoacids;

d) a —$COR_a$ or $COR_8$ group in which $R_a$ is the terminal amino group of a peptidyl residue containing from 1 to 3 aminoacids and $R_8$ is $C_1$–$C_4$ alkoxy unsubstituted or substituted by phenyl or $R_8$ is a —$(CH_2)_n NH_2$, —$(CH_2)_n$—$NR_4R_5$ or —$(CH_2)_n$—$NHR_6$ group in which n is 1 or 2 and $R_4$, $R_5$ and $R_6$ are as defined above;

e) a —Y—CO—Y'—$R_9$ group wherein each of Y and Y' which may be the same or different is —NH— or —O— and $R_9$ is phenyl or $C_1$–$C_6$ alkyl unsubstituted or substituted by phenyl; and f) a —$NHR_6$ or —$NHR_{10}$ group in which $R_6$ is as defined above and $R_{10}$ is $C_1$–$C_6$ alkyl substituted by 1 to 3 hydroxy groups;

and the others are independently chosen from hydrogen, halogen, amino, hydroxy, $C_1$–$C_6$ alkyl, $C_1$–$C_6$ alkoxy, carboxy, $C_1$–$C_6$ alkoxy-carbonyl, $C_2$–$C_6$ alkanoyloxy, cyano and —$NR_4R_5$ in which $R_4$ and $R_5$ are as defined above, or a pharmaceutically acceptable salt of formula (I).

2. A compound of formula (I), according to claim 1, wherein one of R, $R_1$, $R_2$ and $R_3$ is independently a substituent selected from:

a') —X—$(CH_2)_m$—$NH_2$, —X—$(CH_2)_m$—$NR_4R_5$ or —X—$(CH_2)_m NHR_6$ in which X is oxygen or —NH—, m is 1 or 2, one of $R_4$ and $R_5$ is $C_1$–$C_4$ alkyl and the other is hydrogen or $C_1$–$C_4$ alkyl or $R_4$ and $R_5$ taken together with the nitrogen atom to which they are linked form a pyrrolidine or piperidine ring, and $R_6$ is $C_2$–$C_4$ alkanoyl or the terminal carbonyl group of a peptidyl residue containing 1 or 2 aminoacids;

b') —NHC(NH)$NH_2$ or —N=CH—$NR_4R_5$ in which one of $R_4$ and $R_5$ is $C_1$–$C_4$ alkyl and the other is hydrogen or $C_1$–$C_4$ alkyl;

c') —X—$(CH_2)_m$—$COR_7$ in which X is —O— or —NH—, m is 1 or 2, $R_7$ is hydroxy, $C_1$–$C_4$ alkoxy, amino or $R_7$ is the terminal amino group of a peptidyl residue containing 1 or 2 aminoacids;

d') a —$COR_1$ or —$COR_8$ group in which $R_8$ is as defined above and $R_8$ is $C_1$–$C_4$ alkoxy unsubstituted or substituted by phenyl or $R_8$ is —$(CH_2)_n$—$NH_2$ or —$(CH_2)_n$—$NR_4R_5$ in which n is 1 or 2 and one of $R_4$ and $R_5$ is $C_1$–$C_4$ alkyl and the other is hydrogen or $C_1$–$C_4$ alkyl or $R_4$ and $R_5$ taken together with the nitrogen atom to which they are linked form a pyrrolidine or piperidine ring; and e') —$NHR_6$ or —$NHR_{10}$ in which $R_6$ is $C_2$–$C_4$ alkanoyl or the terminal carbonyl group of a peptidyl residue containing 1 or 2 aminoacids and $R_{10}$ is $C_1$–$C_4$ alkyl substituted by one or two hydroxy groups;

and the others are independently chosen from hydrogen, halogen, amino, hydroxy, $C_1$–$C_4$ alkyl, $C_1$–$C_4$ alkoxy, $C_2$–$C_4$ alkoxycarbonyl, $C_2$–$C_4$ alkanoyloxy, cyano, $C_1$–$C_4$ alkylamino or di($C_1$–$C_4$ alkyl)-amino; or a pharmaceutically acceptable salt of formula (I).

3. A compound selected from:

5-aminomethylcarbonyl-3-(indol-3-yl-methylene)-2-indolinone;

3-(indol-3-ylmethylene)-5-(2-piperidin-1-yl-acetyl)-2-indolinone;

5-(2,3-dihydroxy-propylamino)-3-(5-methoxy-indol-3-yl methylene)-2-indolinone;

3-(5-dimethylaminomethyleneamino-indol-$^2$-yl methylene)-2-indolinone;

N-[3-(5-bromo-2-indolinone-3-ylidenemethyl)-indol-5-yl]guanidine;

6-L-alanylamino-[3-(5-methoxy-indol-3-ylmethylene)-2-indolinone); 5-alanylamino-3-((5'-methoxy-3'-indolyl) methylene)-2-indolinone; and 5-L-glutamyl-L-alanylamino-3-[(51-methoxy-3'-indolyl) methylene]-2-indolinone;

which, when appropriate, may be either a Z- or diastereoisomer or Z,E-mixtures of said -d astereoisomers;

or a pharmaceutically acceptable salt thereof.

4. A process for the preparation of a compound of formula (I), according to claim 1, or a pharmaceutically acceptable salt thereof, the process comprising:

a) reacting an aldehyde of formula (II)

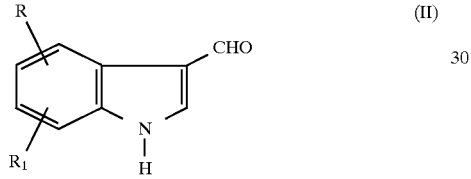

wherein R and $R_1$ are as defined in claim 1, with a compound of formula (III)

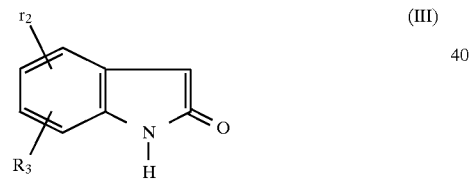

wherein $R_2$ and $R_3$ are as defined in claim 1; or b) reacting a compound of formula (IV)

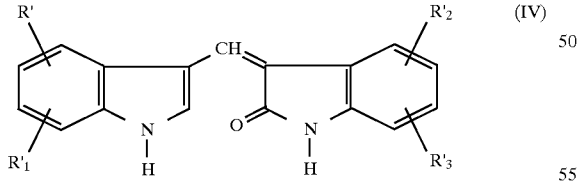

wherein one or two of R', $R'_1$, $R'_2$ and $R'_3$ are —OH, —$NH_2$ or —SH and the others are as R, $R_1$, $R_2$ and $R_3$ as defined in claim 1, with an alkylating agent of formula (V) selected from Z—$(CH_2)_m$—$NH_2$;
Z—$(CH_2)_m$—$NR_4R_5$;
Z—$(CH_2)_m$—$NHR_6$; and
Z—$(CH_2)_m COR_7$ in which Z is a halogen atom and m, $R_4$, $R_5$, $R_6$ and $R_7$ are as defined in claim 1, thus obtaining a compound of formula (I) wherein one or two of R, $R_1$, $R_2$ and $R_3$ are as defined in claim 1 under a) or c); or c) reacting a compound of formula (VI)

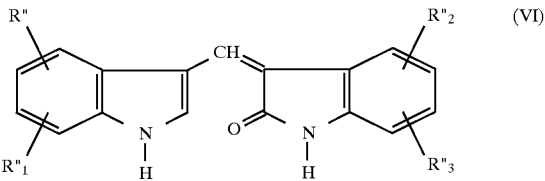

wherein one or two of R", $R''_1$, $R''_2$ and $R''_3$ are —OH or —$NH_2$ and the others are as R, $R_1$, $R_2$ and $R_3$ as defined in claim 1, with an acylating agent of formula (VII) selected from
HOOC—Y'—$R_9$;
HOOC—$R_a$;
HOOC—$R_8$;

or a reactive carbonyl derivative thereof wherein $R_a$, $R_8$, Y' and $R_9$ are as defined in claim 1, thus obtaining a compound of formula (I) wherein one or two of R, $R_1$, $R_2$ and $R_3$ are as defined in claim 1 under d) or e); and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers.

5. A pharmaceutical composition containing a suitable carrier or diluent and, as an active principle, a compound of formula (I), according to claim 1, or a pharmaceutically acceptable salt thereof.

6. A method for inhibiting a tyrosine kinase comprising contacting the compound according to claim 1 or a pharmaceutically acceptable salt thereof with a tyrosine kinase for a period of time sufficient to inhibit said tyrosine kinase.

7. A method for inhibiting proliferation of cells comprising contacting the compound or salt, as claimed in claim 1 with the cells for a period of time and in an amount sufficient to inhibit the proliferation of the cells.

8. A method for inhibiting metastasis comprising administering to an organism in need thereof an amount of the compound or salt, as claimed in claim 1 sufficient to inhibit metastasis.

9. A method for inhibiting development of an atheromatous plaque comprising administering to an organism in need thereof an amount of the compound or a salt, as claimed in claim 1 sufficient to inhibit the development of the atheromatous plaque.

10. Products containing a compound of formula (I), as defined in claim 1, or a pharmaceutically acceptable salt thereof, and an additional anti-tumor agent.

11. A method for inhibiting angiogenesis comprising administering to an organism in need thereof an amount of the compound of claim 1 sufficient to inhibit angiogenesis.

12. A method of providing immunomodulation to an organism comprising administering to an organism in need thereof an amount of the compound of claim 1 sufficient to provide immunomodulation.

* * * * *